US012655086B2

(12) United States Patent
Kim et al.

(10) Patent No.: US 12,655,086 B2
(45) Date of Patent: Jun. 16, 2026

(54) METHOD FOR PREPARING ESTER-BASED COMPOSITION

(71) Applicant: LG CHEM, LTD., Seoul (KR)

(72) Inventors: Hyun Kyu Kim, Daejeon (KR); Jeong Ju Moon, Daejeon (KR); Eun Suk Kim, Daejeon (KR); Yun Gon Heo, Daejeon (KR); Joo Ho Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 656 days.

(21) Appl. No.: 18/016,198

(22) PCT Filed: Sep. 17, 2021

(86) PCT No.: PCT/KR2021/012895
§ 371 (c)(1),
(2) Date: Jan. 13, 2023

(87) PCT Pub. No.: WO2022/065852
PCT Pub. Date: Mar. 31, 2022

(65) Prior Publication Data
US 2023/0303476 A1 Sep. 28, 2023

(30) Foreign Application Priority Data

Sep. 24, 2020 (KR) ........................ 10-2020-0124125
Sep. 17, 2021 (KR) ........................ 10-2021-0124974

(51) Int. Cl.
| | |
|---|---|
| *C07C 67/08* | (2006.01) |
| *B01J 19/24* | (2006.01) |
| *B01J 31/12* | (2006.01) |
| *C07C 69/80* | (2006.01) |

(52) U.S. Cl.
CPC ............. *C07C 67/08* (2013.01); *B01J 19/242* (2013.01); *B01J 31/12* (2013.01); *C07C 69/80* (2013.01)

(58) Field of Classification Search
CPC ........ C07C 67/08; C07C 69/80; B01J 19/242; B01J 31/12; B01J 2231/49; B01J 31/0212
See application file for complete search history.

(56) References Cited

U.S. PATENT DOCUMENTS

| | | | |
|---|---|---|---|
| 4,675,434 A | 6/1987 | Uhm et al. | |
| 5,296,587 A | 3/1994 | Sumner, Jr. et al. | |
| 5,532,405 A * | 7/1996 | Lyford, IV ............. | C07C 67/08 |
| | | | 560/204 |
| 6,235,924 B1 | 5/2001 | McConnell et al. | |
| 6,355,817 B1 * | 3/2002 | Woods .................... | C07C 67/08 |
| | | | 554/170 |
| 7,799,942 B2 | 9/2010 | Osborne et al. | |
| 7,816,554 B2 | 10/2010 | Sutton et al. | |
| 2004/0030175 A1 | 2/2004 | Disteldorf et al. | |
| 2007/0129565 A1 | 6/2007 | Sutton et al. | |

| | | | |
|---|---|---|---|
| 2010/0137631 A1 | 6/2010 | De Munck et al. | |
| 2011/0251420 A1 | 10/2011 | Disteldorf et al. | |
| 2011/0301377 A1 | 12/2011 | Peters et al. | |
| 2014/0148612 A1 | 5/2014 | De Munck et al. | |
| 2015/0141691 A1 | 5/2015 | Disteldorf et al. | |
| 2016/0264509 A1 | 9/2016 | Kaller et al. | |
| 2017/0267813 A1 | 9/2017 | Moon et al. | |
| 2019/0127521 A1 | 5/2019 | Hwang et al. | |
| 2019/0263745 A1 | 8/2019 | Lee et al. | |
| 2021/0317063 A1 | 10/2021 | Lee et al. | |

FOREIGN PATENT DOCUMENTS

| | | | | |
|---|---|---|---|---|
| CN | 102186806 A | 9/2011 | | |
| CN | 102256923 A | 11/2011 | | |
| CN | 110114336 A | 8/2019 | | |
| EP | 2609068 B1 | 3/2020 | | |
| JP | S62-164647 A | 7/1987 | | |
| JP | 3300356 B2 | 7/2002 | | |
| JP | 2012512231 A * | 5/2012 | ............. | C07C 67/08 |
| JP | 2015-160814 A | 9/2015 | | |
| JP | 2018052993 A * | 4/2018 | | |
| KR | 10-2003-0048469 A | 6/2003 | | |
| KR | 10-2003-0068182 A | 8/2003 | | |
| KR | 10-1354141 B1 | 1/2014 | | |
| KR | 10-2014-0077342 A | 6/2014 | | |
| KR | 10-2016-0024698 A | 3/2016 | | |
| KR | 10-1663586 B1 | 10/2016 | | |
| KR | 10-2018-0035522 A | 4/2018 | | |
| KR | 10-2019-0027623 A | 3/2019 | | |
| KR | 10-2020-0063577 A | 6/2020 | | |
| WO | 2005/051885 A1 | 6/2005 | | |
| WO | 2008/110306 A1 | 9/2008 | | |

OTHER PUBLICATIONS

Machine translations of JP 2018-052993A (Year: 2018).*
Machine translations of JP 2012-512231A (Year: 2012).*
Office Action issued in corresponding Japanese patent application 2023-501850 dated Dec. 25, 2023.
Rahman et al., "The plasticizer market: an assessment of traditional plasticizers and research trends to meet new challenges," Progress in Polymer Science, 29: 1223-1248 (2004).
Janjua et al., "Systemic Uptake of Diethyl Phthalate, Dibutyl Phthalate, and Butyl Paraben Following Whole-Body Topical Application and Reproductive and Thyroid Hormone Levels in Humans," Environmental Science and Technology, 41: 5564-5570 (2007).
International Search Report (with partial translation) and Written Opinion dated Dec. 28, 2021, for corresponding International Patent Application No. PCT/KR2021/012895.
Extended European Search Report issued Mar. 21, 2024 for European Patent Application No. 21872880.6.

(Continued)

*Primary Examiner* — Deborah D Carr
(74) *Attorney, Agent, or Firm* — Morgan, Lewis & Bockius LLP

(57) ABSTRACT

The present invention relates to a method for continuously preparing an ester-based composition, the method increasing a preparation yield by optimizing pressure of a reactor as a process variable of each reactor of a reaction unit in which a plurality of reactors are connected in series.

11 Claims, No Drawings

(56) References Cited

OTHER PUBLICATIONS

Office Action issued in corresponding Taiwanese Patent Application No. 110135134 dated Nov. 25, 2024.

Pre-Appeal Examination Report issued in corresponding Japanese Patent Application No. 2023-501850 dated Jan. 14, 2025.

Office Action dated Aug. 8, 2024 issued in corresponding Chinese patent application No. 202180060094.

Office Action issued in corresponding Indian Patent Application No. 202317010118, dated Mar. 26, 2026.

* cited by examiner

METHOD FOR PREPARING ESTER-BASED COMPOSITION

TECHNICAL FIELD

Cross-reference to Related Applications

This application claims the benefit of Korean Patent Application Nos. 10-2020-0124125, filed on Sep. 24, 2020, and 10-2021-0124974, filed on Sep. 17, 2021, in the Korean Intellectual Property Office, the disclosures of which are incorporated herein in their entireties by reference.

TECHNICAL FIELD

The present invention relates to a preparation method increasing a preparation yield of an ester-based composition by optimizing process variables of a plurality of series-connected reactors.

BACKGROUND ART

Phthalate-based plasticizers had accounted for 92% of the global plasticizer market by the 20th century (see Mustafizur Rahman and Christopher S. Brazel, "The plasticizer market: an assessment of traditional plasticizers and research trends to meet new challenges", Progress in Polymer Science 2004, 29, 1223-1248), and are additives used for imparting flexibility, durability, and cold resistance mainly to polyvinyl chloride (hereinafter referred to as PVC) and lowering the viscosity during melting to improve processability. These phthalate-based plasticizers are added in various amounts to PVC and widely used in various applications from rigid products such as rigid pipes to soft products which may be used for such as food packaging materials, blood bags, flooring materials, etc. due to their soft and good flexibility, and thus are more closely related to real life than any other material, and the direct contact with the human body may not avoidable.

However, despite the compatibility of the phthalate-based plasticizers with PVC and their excellent capability to impart flexibility, it has been argued recently about harmfulness of the PVC product containing the phthalate-based plasticizers that the phthalate-based plasticizers may leak out of the PVC product when used in real life, and act as a presumed endocrine disrupting (environmental hormone) substance and a carcinogen of the level of heavy metals (see N. R. Janjua et al., "Systemic Uptake of Diethyl Phthalate, Dibutyl Phthalate, and Butyl Paraben Following Whole-body Topical Application and Reproductive and Thyroid Hormone Levels in Humans", Environmental Science and Technology 2007, 41, 5564-5570). Especially, since the report about the leakage of di-(2-ethyl hexyl) phthalate (DEHP), which was the most used phthalate-based plasticizer in the US in the 1960s, out of the PVC product, the interest in environmental hormones has been added in the 1990s and global environmental regulations as well as extensive studies on hazards of the phthalate-based plasticizers to human have started.

Therefore, in order to cope with environmental hormone problems and environmental regulations due to the leakage of the phthalate-based plasticizers, a number of researchers have been conducting research to develop a new, alternative, non-phthalate-based plasticizer which is free of phthalic anhydride used in the production of phthalate-based plasticizers or a leakage inhibition technology which may inhibit the leakage of the phthalate-based plasticizers to greatly reduce the hazards to human and be in accordance with environmental standards.

Meanwhile, as a non-phthalate-based plasticizer, a terephthalate-based plasticizer has been getting the spotlight, because it is equivalent to the phthalate-based plasticizer in terms of physical properties, but is free of environmental issues. A variety of terephthalate-based plasticizers have been developed and researched on the development of a terephthalate-based plasticizer having excellent physical properties, as well as researched on facilities for preparing such the terephthalate-based plasticizer have been actively conducted. In terms of process design, more efficient, economical, and simple process design has been required.

RELATED ART DOCUMENT (Patent Document 1) Korean Patent Laid-Open Publication No. 10-1354141

(Non-patent Document 1) Mustafizur Rahman and Christopher S. Brazel "The plasticizer market: an assessment of traditional plasticizers and research trends to meet new challenges" Progress in Polymer Science 2004, 29, 1223-1248

(Non-patent Document 2) N. R. Janjua et al. "Systemic Uptake of Diethyl Phthalate, Dibutyl Phthalate, and Butyl Paraben Following Whole-body Topical Application and Reproductive and Thyroid Hormone Levels in Humans" Environmental Science and Technology 2007, 41, 5564-5570

DISCLOSURE OF THE INVENTION

Technical Problem

The present invention is to provide an efficient method for preparing an ester-based composition, and provide a method for efficiently and continuously preparing an ester-based composition by arranging a plurality of reactors in series and optimizing process variables of each reactor.

Technical Solution

To solve the tasks, the present invention provides a method for preparing an ester-based composition.

(1) There is provided a method for preparing an ester-based composition, the method including: putting polycarboxylic acid and at least one mono-alcohol having 3 to 12 alkyl carbon atoms into a mixer to form a reaction mixture (S1); and continuously putting the reaction mixture into a reaction unit in which a total of N reactors are connected in series from a first reactor to an N-th reactor to continuously produce reaction products (S2), wherein Expressions 1 and 2 below are satisfied:

$$P_{n1} \leq P_{n1-1} \qquad \text{[Expression 1]}$$

$$P_1 > P_N \qquad \text{[Expression 2]}$$

In Expressions 1 and 2 above, $P_x$ is a pressure of an x-th reactor, n1 above is an integer of 2 to N, and N above is an integer of 3 or more.

(2) The present invention provides the method according to (1) above, wherein the step S2 further satisfies Expression 3 below:

$$E_1 \leq E_{n1} \qquad \text{[Expression 3]}$$

3

In Expression 3 above, $$E_x = [\{\text{Number of moles of mono-alcohol put into the } x\text{-th reactor} - (c*\text{Number of moles of polycarboxylic acid put into the } x\text{-th reactor})\}/ (c*\text{Number of moles of polycarboxylic acid put into the first reactor})]*100\%$$

c is the number of carboxylic acid groups contained in one molecule of the polycarboxylic acid, and n1 and N above are as defined above.

(3) The present invention provides the method according to (1) or (2) above, wherein the step of S2 further satisfies Expression 4 below:

$$T_m \leq T_1 \leq T_{n1} \qquad \text{[Expression 4]}$$

In Expression 4 above, $T_m$ is a temperature of the mixer, $T_x$ is a temperature of the x-th reactor, n1 and N above are as defined above.

(4) The present invention provides the method according to any one of (1) to (3) above, wherein the method further includes at least one step selected from the group consisting of: adding a catalyst to the reaction mixture between the step S1 and the step S2 (S1-1), adding a catalyst to a polycarboxylic acid and alcohol before the step S1 (S1-2), and adding a catalyst to the first reactor of the step S2 (S2a).

(5) The present invention provides the method according to any one of (1) to (4) above, wherein the method further includes adding a catalyst to at least one reactor selected from among the second to N-th reactors of the step S2 (S2b).

(6) The present invention provides the method according to any one of (1) to (5) above, wherein the catalyst is tetraalkyl titanate.

(7) The present invention provides the method according to any one of (1) to (6) above, wherein $P_1$ is 0.3 barg to 1.0 barg, and $P_N$ is 0 barg to 0.5 barg.

(8) The present invention provides the method according to any one of (1) to (7) above, wherein $E_1$ is 0 to 100%, and $E_N$ is 0 to 200%.

(9) The present invention provides the method according to any one of (1) to (8) above, wherein $T_m$ is 20 to 200° C., $T_1$ is 150 to 230° C., and $T_N$ is 180 to 250° C.

(10) The present invention provides the method according to any one of (1) to (9) above, wherein N above is an integer of 3 to 5.

(11) The present invention provides the method according to any one of (1) to (10) above, wherein the method further includes: continuously moving the reaction products into a separation unit to remove unreacted alcohol (S3); and putting the unreacted alcohol removed from the separation unit back into at least one reactor selected from among the reactors of the reaction unit (S4).

(12) The present invention provides the method according to any one of (1) to (11) above, wherein the method further includes putting at least one mono-alcohol having 3 to 12 alkyl carbon atoms into the reaction products from which the unreacted alcohol is removed to perform a trans-esterification reaction (S5), wherein the alcohol input in the step S5 is different from the alcohol input in the step S1.

(13) The present invention provides the method according to any one of (1) to (12) above, wherein the polycarboxylic acid is at least one selected from the group consisting of a dicarboxylic acid, a tricarboxylic acid, and a tetracarboxylic acid.

(14) The present invention provides the method according to any one of (1) to (13) above, wherein: the dicarboxylic acid is at least one selected from the group consisting of a linear dicarboxylic acid having 2 to 10 carbon atoms, a terephthalic acid, a phthalic anhydride, an isophthalic acid, a cyclohexane dicarboxylic acid, an anhydride thereof, and a derivative thereof; the tricarboxylic acid is at least one selected from the group consisting of a citric acid, a trimellitate acid, a cyclohexane tricarboxylic acid, an anhydride thereof, and a derivative thereof; and the tetracarboxylic acid is at least one selected from the group consisting of a benzenetetracarboxylic acid, a furantetracarboxylic acid, a cyclohexane tetracarboxylic acid, a tetrahydrofuran tetracarboxylic acid, an anhydride thereof, and a derivative thereof.

Advantageous Effects

A preparation method of the present invention may enable an efficient preparation of an ester-based composition by designing a process to continuously use a plurality of reactors arranged in series, and optimizing process variables, specifically, pressure, of each reactor arranged in series.

MODE FOR CARRYING OUT THE INVENTION

Hereinafter, the present invention will be described in more detail.

It will be understood that words or terms used in the specification and claims of the present invention shall not be construed as being limited to having the meaning defined in commonly used dictionaries. It will be further understood that the words or terms should be interpreted as having meanings that are consistent with their meanings in the context of the relevant art and the technical idea of the invention, based on the principle that an inventor may properly define the meaning of the words or terms to best explain the invention.

In the preparation method of the present invention, a polycarboxylic acid refers to a compound having two or more carboxylic acid groups, and may indicate, for example, a dicarboxylic acid, a tricarboxylic acid, or a tetracarboxylic acid. A polycarboxylic acid used in the present invention may have 2 to 5 carboxylic acid groups, 2 to 4 carboxylic acid groups, or 2 to 3 carboxylic acid groups. When a polycarboxylic acid has too many carboxylic acid groups, the polycarboxylic acid may not be well applied to the preparation method or a preparation system of the present invention due to a high molecular weight of the polycarboxylic acid itself. The polycarboxylic acid is preferably a dicarboxylic acid, a tricarboxylic acid or a tetracarboxylic acid particularly, and the dicarboxylic acid may be at least one selected from the group consisting of a linear dicarboxylic acid having 2 to 10 carbon atoms, a terephthalic acid, a phthalic anhydride, an isophthalic acid, and a cyclohexane dicarboxylic acid, the tricarboxylic acid may be at least one selected from the group consisting of a citric acid, a trimellitate anhydride, and a cyclohexane tricarboxylic acid, and the tetracarboxylic acid may be at least one selected from the group consisting of a benzenetetracarboxylic acid, a furantetracarboxylic acid, a cyclohexane tetracarboxylic acid, and a tetrahydrofuran tetracarboxylic acid. In addition, the polycarboxylic acid may not only include itself, but also include an anhydride or a derivative thereof.

In the preparation method of the present invention, monoalcohol having 3 to 12 alkyl carbon atoms may be preferably at least one selected from the group consisting of propanol, butanol, pentanol, hexanol, heptanol, octanol, nonanol, decanol, undecanol, and dodecanol, all of which are of a linear type or a branched type, and more preferably, may be at least one of alcohols having 4 to 10 carbon atoms. In addition, the alcohol may be a single type of alcohol, or may be in the form of a mixture containing isomers having the same number of carbon atoms. For example, when the alcohol is alcohol having 3 alkyl carbon atoms, the alcohol may be 1-propanol or 2-propanol, or may be in the form of a mixture containing 1-propanol and 2-propanol in a certain ratio. When the alcohol is in the form of a mixture containing isomers having the same number of carbon atoms, the relative amount of each isomer is not particularly limited. Meanwhile, in the alcohol used in the present invention, "mono" indicates that one hydroxyl group is present in one molecule of alcohol.

Method for Preparing Ester-Based Composition

There is provided a method for preparing an ester-based composition, the method including: putting polycarboxylic acid and at least one mono-alcohol having 3 to 12 alkyl carbon atoms into a mixer to form a reaction mixture (S1), and continuously putting the reaction mixture into a reaction unit in which a total of N reactors are connected in series from a first reactor to an N-th reactor to continuously produce reaction products (S2), wherein Expressions 1 and 2 below are satisfied:

$$P_{n1} \leq P_{n1-1} \tag{Expression 1}$$

$$P_1 > P_N \tag{Expression 2}$$

In Expressions 1 and 2 above,
$P_x$ is a pressure of an x-th reactor,
n1 above is an integer of 2 to N, and
N above is an integer of 3 or more.

Hereinafter, each step included in the preparation method of the present invention will be described in more detail.

Mixing Step (S1)

The preparation method of the present invention includes putting polycarboxylic acid and at least one mono-alcohol having 3 to 12 alkyl carbon atoms into a mixer to form a reaction mixture (S1).

Specifically, the step S1 of forming the reaction mixture refers to a step of uniformly mixing the polycarboxylic acid and at least one mono-alcohol having 3 to 12 alkyl carbon atoms in a mixer. In the present step, before the polycarboxylic acid and at least one mono-alcohol having 3 to 12 carbon atoms, which correspond to reaction raw materials, are put into a reactor, the polycarboxylic acid and at least one mono-alcohol having 3 to 12 carbon atoms are uniformly pre-mixed in the mixer to prevent an issue which may occur when the raw materials are directly put into the reactor without being pre-mixed, for example, a non-uniform reaction issue of varying conversion rates depending on the position inside the reactor.

Meanwhile, in an esterification reaction, the reaction occurs theoretically in a molar ratio of 1 mol of carboxyl group to 1 mol of hydroxy group, and when the polycarboxylic acid is a dicarboxylic acid, the reaction occurs in a molar ratio of 1:2, and when the polycarboxylic acid is a tricarboxylic acid, the reaction occurs in a molar ratio of 1:3. Accordingly, the theoretical amount of polycarboxylic acid and mono-alcohol added as raw materials may be in a molar ratio of 1:2 to 1:8 with respect to divalent to tetravalent carboxylic acids.

However, such molar ratios are ranges that satisfy a minimum amount required for the reaction, and the amount of alcohol actually added may be greater than the minimum amount ranges to achieve conversion rates of the reaction and control minimum residence time. More specifically, the mono-alcohol may be added in an amount of more than 20 mol % to 100 mol % relative to the polycarboxylic acid equivalent with respect to the amount added to the mixer. In the present invention, that the mono-alcohol is added in excess relative to the polycarboxylic acid equivalent indicates that greater than the amount of the mono-alcohol required to make the entire amount of the polycarboxylic acid react, that is an excess amount relative to the equivalent is added. More specifically, for example, that the mono-alcohol is added in more than 60 mol % relative to the polycarboxylic acid equivalent indicates that the mono-alcohol is added in 160 mol % of the equivalent. In the present invention, the amount of mono-alcohol added in excess may be 20 mol % or more, 30 mol % or more, 40 mol % or more, or 50 mol % or more, and may be 100 mol % or less, 90 mol % or less, 80 mol % or less, or 70 mol % or less relative to the polycarboxylic acid equivalent. When the excess amount of mono-alcohol is within the ranges described above, effects resulting from pressure control through Expressions 1 and 2, which will be described later, may be maximized. In particular, in applying the preparation method of the present invention, when the amount of mono-alcohol added in excess is 20 mol % to 60 mol % relative to the polycarboxylic acid equivalent, energy use may be improved to maximum, and when the amount thereof is 40 mol % to 100 mol %, productivity may also be further improved to maximum. Meanwhile, in the above descriptions, the amount of mono-alcohol added in excess is the same as E value, which will be described later.

In addition, the mono-alcohol is added in excess, and thus, other than being put into the mixer in the present step S1, the mono-alcohol may be put directly into a reactor also during the reaction. This will be described in more detail in the step S2, which will be described later.

Reaction Step (S2)

The method for preparing an ester-based composition of the present invention includes continuously putting the reaction mixture into a reaction unit in which N reactors are connected in series to perform a reaction, thereby continuously producing reaction products from the reaction unit (S2).

In the present invention, an esterification reaction is performed using a plurality of reactors connected in series. When a reaction unit not having just one reactor but having a plurality of reactors connected in series is used, a smaller reactor may be used compared to a case in which one reactor is used, so that the space design of a process is easy, thereby reducing design costs, and since reaction raw materials continuously pass though the plurality of reactors connected in series, process variables for each reactor may be independently controlled to allow the optimization of the entire process, thereby maximizing the efficiency of the preparation process.

In addition, the step S2 in the preparation method of the present invention may satisfy Expressions 1 and 2:

$$P_{n1} \leq P_{n1-1} \tag{Expression 1}$$

$$P_1 > P_N \tag{Expression 2}$$

In Expressions 1 and 2 above,
$P_x$ is a pressure of the x-th reactor,
n1 above is an integer of 2 to N, and
N above is an integer of 3 or more.

The inventor of the present invention has found that it is possible to optimize a continuous ester-based composition preparation process by controlling the temperature of each reactor to satisfy Expressions 1 and 2 above in the step S2. Particularly, the inventor of the present invention has confirmed that when the above Expressions are satisfied, the amount of an ester-based composition to be prepared may be maximized and the amount of the composition to be prepared per unit time may also be maximized while the amount of wasted reaction raw materials is minimized.

More specifically, the reaction temperature at which the esterification reaction is performed is a temperature equal to or above the boiling point of mono-alcohol, and as the reaction proceeds, a portion of the mono-alcohol is not involved in the reaction and is vaporized, and at the same time, water is generated as a reaction by-product and the water forms an azeotropic state with the mono-alcohol and is refluxed to an upper portion of the reactor. Such a reflux process is inevitable upon the esterification reaction, and how the reflux process is controlled may greatly affect reaction productivity and energy efficiency.

In such reaction conditions, when the esterification reaction is performed under pressure by increasing the pressure at an early stage of reaction, the vaporized alcohol may be retained at the site where the reaction takes place in the reactor to some extent, thereby leading to accelerated reaction rates and reduced reflux amount to increase energy efficiency. Therefore, in the present invention, a first reactor is set to have a highest pressure and a last N-th reactor is set to have a lowest pressure, and the pressure is set to be lowered towards a subsequent reactor from a preceding reactor, or is set to be maintained the same to tackle the issues described above.

In addition, according to an embodiment of the present invention, when the reaction is performed under pressure by increasing the pressure in the first reactor as $P_1$ is set to 0.3 barg to 1.0 barg, the vaporization of alcohol occurring at the beginning of reaction is suppressed as much as possible and the amount of water present in the reactor is small at the early stage of reaction, and thus the issues described above are hardly seen.

However, when $P_1$ is set to less than 0.3 barg, the reflux of mono alcohol is hardly suppressed, and thus a significant amount of alcohol is vaporized and refluxed, and this causes a great deal of energy use while a condenser and a bed separator are circulated from the reactor, and further due to such a reflux circulation, an absolute amount of alcohol required to be present and involved in the reaction is lost to deteriorate reactivity, and an additional input of alcohol to make up for the loss may cause an additional loss of energy, resulting in a continuous vicious cycle.

In addition, when $P_1$ is set to greater than 1.0 barg, reflux is suppressed as much as possible and the amount of alcohol present in the reactor increases, but at the same time, water generated as a reaction product also increases, thereby inducing a reverse reaction to reach a reversible reaction state at a certain level, causing a significant reduction in forward reaction rate. To prevent the above issues and increase reaction rate and energy efficiency, $P_1$ may be controlled to 0.3 barg to 1.0 barg, preferably 0.4 to 1.0 barg, particularly preferably 0.4 to 0.8 barg.

Meanwhile, as for pressure control in the reactor as described above, as the reaction proceeds, pressure may need to be weakened, or completely released. When the reaction is performed only under pressure upon the reaction process, water, a by-product of the reaction stays longer in the reactor, and when the water is not removed, the reaction may not be performed well in the forward reaction direction, resulting in reduced reaction rate. In addition, a catalyst is sensitive to water, and thus the catalyst may be deactivated. As such, setting a high reaction pressure in the esterification reaction does not solely bring about reaction improvement, but results in both improvement and deterioration together.

Accordingly, taking the progress of the reaction, and the advantages and disadvantages of the pressure control described above into account, pressure reduction compared to the preceding reactor or complete release of pressure in subsequent reactors including the second reactor may be performed, and such pressure reduction or pressure release may be performed in the subsequent reactors including the second reactor.

For example, when the reaction is performed through a total of four reactors, pressure reduction or pressure release may be performed in the second reactor, the third reactor, or the fourth reactor, and more specifically, when the pressure reduction is performed only in the second reactor, the pressure in the reactor may be the highest in the first reactor and may be maintained the same in the second to fourth reactors. Meanwhile, when the pressure is reduced in both the second reactor and the third reactor, the pressure in the first reactor may be the highest, the pressure in the second reactor may be the second highest, and the pressures in the third reactor and the fourth reactor may be the same. In addition, when the pressure release is performed only in the fourth reactor, the pressures in the first to third reactors may all be the same, but only the pressure in the fourth reactor may be lower than the pressures in the preceding reactors. Taken together, this suggests that the pressure reduction or the pressure release may be performed in the conditions in which Expressions 1 and 2 described above are satisfied, and in the present invention, the order of reactors in which pressure reduction or pressure release is performed, the number of pressure reduction, and the like may be appropriately selected in consideration of overall reaction conditions.

As described above, when the pressure reduction or the pressure release is performed, the pressure in the last reactor shows a minimum value among the pressures of all reactors, and in this case, more specifically, the pressure in the last reactor may be −0.3 barg to 0.5 barg, more preferably −0.3 barg to 0.4 barg. Meanwhile, that the reactor pressure is negative indicates that the pressure has been reduced by an absolute value of the negative number relative to atmospheric pressure. That the pressure in the last reactor is within the ranges described above indicates that preferably the pressure in the reactor at the latter stage of reaction is set to be lower than the pressure at the early stage of reaction, and the pressure in the last reactor is set at least at atmospheric level, or at atmospheric to slightly reduced pressure levels (about 200 torr). Applying pressure is less needed at the latter stage of reaction compared to the early stage of reaction, and applying pressure at some extent may be effective in removing a certain amount of generated water, and due to the addition of an excess amount of mono-alcohol, the amount of mono-alcohol remaining in the reactor may be higher than the equivalent even when a certain portion is refluxed, and thus, the removal of water may make a more significant contribution. In addition, as a catalyst serves a more important role towards the latter stage of reaction, preventing deactivation of the catalyst while continuously removing water may also be critical. Accordingly, the pressure in the last reactor may be preferably at least atmospheric level (0 barg). Meanwhile, in the last reactor, little polycarboxylic acid is present, whereas a large amount of alcohol is present, and to remove such alcohol, the pressure in the reactor may be set to be slightly lower than the atmospheric pressure, and thus, both reacted and unreacted alcohol may be distilled together. For such purpose, the pressure in the last reactor may be preferable between 0 barg and −0.3 barg. When the pressure in the last reactor is controlled within the ranges described above, the previously discussed concerns may be minimized, and reaction improvement according to the pressure control may be maximized.

Meanwhile, the step S2 may satisfy Expression 3 below:

$$E_1 \leq E_{n1} \qquad \text{[Expression 3]}$$

In Expression 3 above, $E_x$=[{Number of moles of mono-alcohol put into the x-th reactor–($c$*Number of moles of polycarboxylic acid put into the x-th reactor)}/ ($c$*Number of moles of polycarboxylic acid put into the first reactor)]*100% c is the number of carboxylic acid groups contained in one molecule of the polycarboxylic acid, and n1 and N above are as defined above.

In addition to the pressure control in each reactor described above, when controlling an excess amount of alcohol put into each reactor such that Equation 3 above is satisfied, energy consumed for heating the excess alcohol is minimized while a sufficient amount of alcohol remains in the reactor, thereby achieving a high conversion rate.

Specifically, E above indicates one corresponding to an excess input amount of mono-alcohol described in the step S1 above, and more specifically, the E value means, based on the "amount of alcohol required to allow a polycarboxylic acid initially input from a first reactor to be reacted to 100%", the ratio of "the additional input amount of alcohol to the amount of alcohol required to allow a polycarboxylic acid put into each reactor to be reacted to 100%". The amount means an amount based on moles. For example, when a polycarboxylic acid is a dicarboxylic acid, and when the dicarboxylic acid and alcohol are put into a reactor in an amount of 100 moles and in an amount of 300 moles, respectively, the amount of alcohol for allowing the dicarboxylic acid to be reacted to 100% is 200 moles, and thus, the amount of alcohol to be additionally input is 100 moles. Therefore, an E value, which is a ratio thereof, corresponds to 50%, which is a ratio of 100 moles to 200 moles.

The E value is maintained the same in each reactor unless alcohol is removed or additionally input upon the reaction, and when alcohol is additionally put into a subsequent reactor, the E value of the corresponding reactor becomes greater than the E value of the preceding reactor. Conversely, when only alcohol is removed from the subsequent reactor, the E value of the corresponding reactor becomes smaller than the E value of the preceding reactor. Therefore, Expression 3 indicates that alcohol may be additionally put into the remaining reactors except for the first reactor.

As such, there is a benefit that when the excess alcohol is not entirely input in the step S1, and a portion of the alcohol is put into at least one selected from among the subsequent reactors including the second reactor, the amount of energy used to heat all of the excess alcohol put into the first reactor may be reduced, and the alcohol concentration of the subsequent reactor in which relatively less alcohol is present is increased, and thus, the reaction rate at the subsequent reactor may be improved. Meanwhile, in consideration of the total number of reactors, the capacity of each reactor, the total reaction time, and the like, the reactor into which alcohol is additionally put may be selected within a range that may minimize energy use and maintain the reaction rate to maximum, and in that additional input of alcohol at the final stage of reaction is not that effective, it may be preferable not to put additional alcohol into an N-th reactor. More specifically, for example, when three reactors are used, additional alcohol may be put into the second reactor, and when four reactors are used, additional alcohol may be put into the second reactor or the third reactor. In addition, when four reactors are used, additional alcohol may be preferably put into the third reactor to maximize the effect of adding alcohol.

$E_1$ above may be 0% to 10%, and may be 100% or less, 90% or less, 80% or less, 70% or less, or 60% or less. In addition, $E_1$ above may be 0% or more, 10% or more, or 20% or more, and may be 200% or less, 180% or less, 160% or less, 140% or less, 120% or less, or 100% or less. When $E_1$ and $E_N$ are either too low or too high, two reaction raw materials are out of balance, so that some reaction raw materials are wasted, and as a result, a composition may not be prepared in a maximum amount. Particularly, when the $E_1$ value is too high, alcohol is input in excess amount from the beginning, resulting in a large amount of alcohol which may not be involved in a reaction, and when this happens, a desired degree of conversion rate may not be achieved, or too much energy may be consumed to heat the alcohol that is not actually involved in the reaction, so that there may be a problem of deteriorating the efficiency of the entire reaction process.

In addition, the step S2 may satisfy Expression 4 below:

$$T_m \leq T_1 \leq T_{n1} \qquad \text{[Expression 4]}$$

In Expression 4 above, $T_m$ is a temperature of the mixer, $T_x$ is a temperature of the x-th reactor, and n1 and N above are as defined above.

In addition to the pressure control and excess alcohol input in each reactor as described above, when the temperature of a mixer and/or a reactor is controlled to satisfy Expression 4 above, energy use may be minimized while a high final conversion rate may be achieved.

Specifically, as the reaction proceeds, the amount of the remaining polycarboxylic acid and mono-alcohol decreases while the volume of the total reactant is maintained, and thus the temperature inside the reactor is preferably higher towards the subsequent reactor to supply heat required for the reaction. In addition, heating may be performed in a mixer in which raw materials are mixed before the raw materials are put into the reactor, and the heating in the mixer needs to be done to the extent that the raw materials may be sufficiently pre-heated without being vaporized, and thus, the temperature is preferably not higher than that of the reactor. Therefore, taken together, the temperature is preferably maintained at least the same or increased towards the subsequent reactor from the mixer, and accordingly, the temperature of the mixer and each reactor may be preferably controlled to satisfy Expression 4.

In this case, the temperature $T_m$ of the mixer may be 20 to 200° C., preferably 20 to 150° C., the temperature $T_1$ of the first reactor may be 150 to 230° C., preferably 180 to 210° C., the temperature $T_N$ of the last reactor may be 180 to 250° C., preferably, 200 to 240° C. When the temperatures of the mixer, the first reactor, and the N-th reactor are within the ranges described above, the esterification reaction may be well performed, and unnecessary energy consumption may be minimized.

In the preparation method of the present invention, N is preferably an integer of 3 or more, more preferably an integer of 3 to 10, particularly preferably an integer of 3 to 5. When the number of reactors is less than the above, a technical advantage of arranging a plurality of reactors in series may not be prominent, and when the number of reactors is too high, process variable adjustment in each reactor becomes difficult, and costs consumed for relevant apparatuses including the reactors are rather rising, so that it may be inefficient in terms of the costs for the entire process.

Catalyst Addition (S1-1, S1-2, S2a, and/or S2b)

The preparation method of the present invention may further include at least one step selected from the group consisting of: adding a catalyst to the reaction mixture between the step S1 and the step S2 (S1-1), adding a catalyst to a polycarboxylic acid and alcohol before the step S1 (S1-2), and adding a catalyst to the first reactor of the step S2 (S2a).

The steps S1-1, S1-2, and S2a are preparation steps related to a catalyst addition, and may include putting a catalyst into a mixer, mixing the catalyst with reaction raw materials and inputting, or putting the catalyst into a first reactor, and at least one step selected from among these may be performed to put the catalyst into a reaction system. The catalyst may be added in any step, but when added in the step S2a, there may be an advantage in preventing side reactions with the catalyst, and when directly added to raw alcohol, there may be an advantage in overall process efficiency.

In addition, other than the above catalyst addition, the method may include adding a catalyst to at least one reactor selected from among the second to N-th reactors of the step S2 (S2b). In the step S2b, a catalyst is additionally added, and the first reactor has the catalyst in a sufficient amount, there is no need for additional input, but subsequent reactors have an increasing amount of deactivated catalyst, and thus an extra amount of catalyst is added to further improve reactivity. Accordingly, the catalyst may be additionally put into any one or more reactors connected in series from the second reactor to the N-th reactor.

The catalyst used in the preparation method of the present invention may be at least one selected from an acid catalyst such as sulfuric acid, hydrochloric acid, phosphoric acid, nitric acid, para-toluenesulfonic acid, methanesulfonic acid, ethanesulfonic acid, propanesulfonic acid, butanesulfonic acid, alkyl sulfuric acid, metal salt such as aluminum lactate, lithium fluoride, potassium chloride, cesium chloride, calcium chloride, iron chloride, and aluminum phosphate, metal oxide such as heteropolyacid, natural/synthetic zeolite, cation and anion exchange resin, and organic metal such as tetraalkyl titanate and a polymer thereof, and may preferably be tetraalkyl titanate. Examples of the tetraalkyl titanate include TiPT, TnBT, TEHT, and the like. As such, it is preferable to use tetraalkyl titanate as a catalyst, because catalyst by-products that may be generated in subsequent processes are controlled or not generated.

The amount of catalyst to be used may vary depending on the type of catalyst, and for example, a homogeneous catalyst may be used in an amount of 0.01 to 5 parts by weight, 0.01 to 3 parts by weight, 0.1 to 5 parts by weight, or 0.1 to 3 parts by weight with respect to 100 parts by weight of polycarboxylic acid, and a heterogeneous catalyst may be used in an amount of 5 to 200 parts by weight, 5 to 100 parts by weight, 20 to 200 parts by weight, or 20 to 150 parts by weight with respect to 100 parts by weight of polycarboxylic acid. In addition, the amount of the catalyst used may be an amount of catalyst that is added at once in one step selected from among S1-1, S1-2, and S2a described above, or may include up to an amount of catalyst added in the step S2b when the step S2b is included. For example, when the catalyst is divided into steps S1-1 and S2b and added, the total amount of catalyst added in the two steps may be within the ranges described above.

Separation Step (S3) and Re-Input Step (S4)

The preparation method of the present invention may further include continuously moving the reaction products to a separation unit to remove unreacted alcohol (S3); and putting the unreacted alcohol removed from the separation unit back into at least one reactor selected from among the reactors of the reaction unit (S4).

Specifically, the step S3 refers to a step in which reaction products prepared from a N-th reactor, which is a last reactor among the plurality of reactors, are continuously moved to a separation unit, and then unreacted alcohol is removed from the separation unit.

The separation unit used in the step S3 may include at least one separation column. Depending on the number of stages of the separation column included in the separation unit in the preparation method of the present invention, the composition ratio of a composition to be finally prepared may vary. Those skilled in the art may appropriately adjust the number of stages of the separation column included in the separation unit according to the composition ratio or properties of the composition to be prepared. In addition, the separation unit may include a purification tank of a drum type in addition to the separation column. The separation unit may remove the amount of unreacted alcohol included in the reaction products to a level of 30% or less, preferably 20% or less, more preferably 10% or less of the total. Since the unreacted alcohol is removed as described above, the physical properties of an ester-based composition to be prepared may be uniform and excellent.

Specifically, the step S4 refers to a step of putting the unreacted alcohol removed from the separation unit back into at least one reactor among the first reactor to the N-th reactor of the reaction unit to reuse the unreacted alcohol remaining in reaction products. Through the step, the excess alcohol may be collected and reused, thereby improving the economic feasibility of the process.

Trans Reaction Step (S5)

The preparation method of the present invention may further selectively include putting at least one alcohol having 3 to 12 alkyl carbon atoms into the reaction products from which the unreacted alcohol is removed to perform a trans-esterification reaction (S5), wherein the alcohol input in the step is different from the alcohol input in the step S1.

Through the step S5, it is possible to prepare a composition including two or more types of ester compounds. Those skilled in the art may select suitable alcohol according to the type of an ester compound to be included in the composition and perform a trans-esterification reaction. It is preferable that the step S5 is performed after the removal of unreacted alcohol. When the step S5 is performed before the removal of the unreacted alcohol, a trans-esterification reaction with newly input alcohol may not be easily performed due to the remaining unreacted alcohol, and even when the reaction is performed to a certain degree, the alcohol content is too high to deteriorate the efficiency of the reaction. Therefore, it is preferable that the amount of the unreacted alcohol included in the reaction products before the trans-esterification reaction is 10% or less.

Ester-Based Composition Preparation System

The present invention provides a system for preparing an ester-based composition including a mixer in which a reaction mixture of polycarboxylic acid and at least one alcohol having 3 to 12 alkyl carbon atoms is formed, a reaction unit having N number of reactors connected in series in which an esterification reaction of the reaction mixture is performed, a separation unit including at least one separation column for receiving the reaction products and removing unreacted alcohol therefrom, a recovery unit for putting the unreacted alcohol removed from the separation unit back into a reactor of the reaction unit, and a variable control unit for controlling the temperature and pressure of each reactor and the amount of alcohol and catalyst put into the reactor.

The preparation system provided by the present invention may be used to implement the preparation method of the present invention, and each of the components of the system is the same as that described above, and thus, a detailed description thereof will be omitted.

In particular, the variable control unit included in the preparation system of the present invention controls the pressure, alcohol input amount, temperature, and catalyst usage of each reactor, such that Expressions 1 to 4 described above are satisfied, thereby serving to optimize the overall reaction process.

EXAMPLES

Hereinafter, the present invention will be described in more detail with reference to Examples. However, the following Examples are for illustrative purposes only to describe the present invention and are not intended to limit the scope of the present invention.

14

Materials

Phthalic acid was used as polycarboxylic acid, 2-ethylhexanol was used as mono-alcohol, and tetrabutyl titanate was used as a catalyst.

Group 1 Confirmation of the Effect of Pressure Control in a Reaction Unit Including Three Reactors An esterification reaction was performed using a reaction unit in which a total of three reactors were connected in series. An amount of each raw material put into a mixer was such that 2-ethylhexanol was added in excess by $E_1\%$ described in Table 1 below relative to the equivalent, specifically, in Comparative Example 1, phthalic acid and 2-ethylhexanol had a molar flow rate of 1:2.8 and were put into the mixer, and tetrabutyl titanate was put into the mixer at a flow rate of 0.23 wt % relative to the input phthalic acid flow rate to form a reaction mixture. The formed reaction mixture was continuously put into a reaction unit in which three reactors were connected in series, and in each Example/Comparative Example, the amount of catalyst put into the mixer, reactor pressure, E value, and the amount of catalyst put into each reactor are outlined in Table 1 below. Meanwhile, the input amount of catalyst in Table 1 below refers to a value obtained by calculating how much catalyst is relatively put into each mixer or reactor, with respect to 100% of the amount of catalyst (0.23 wt % relative to the flow rate of phthalic acid) initially put into the mixer in Comparative Example 1.

TABLE 1

| | Mixer | First reactor | | | Second reactor | | | Third reactor | | | Catalyst |
|---|---|---|---|---|---|---|---|---|---|---|---|
| | Catalyst (%) | $P_1$ (barg) | $E_1$ (%) | Cat-alyst | $P_2$ (barg) | $E_2$ (%) | Cat-alyst | $P_3$ (barg) | $E_3$ (%) | Cat-alyst | in total |
| Example 1 | 50% | 0.8 | 40 | 0 | 0.4 | 40 | 50% | 0 | 40 | 0 | 100% |
| Example 2 | 50% | 0.8 | 40 | 0 | 0.4 | 40 | 25% | 0.2 | 40 | 25% | 100% |
| Example 3 | 50% | 0.8 | 40 | 0 | 0.4 | 40 | 50% | 0.2 | 40 | 50% | 150% |
| Comparative Example 1 | 100% | 0 | 40 | 0 | 0 | 40 | 0 | 0 | 40 | 0 | 100% |
| Comparative Example 2 | 100% | 0.8 | 40 | 0 | 0.8 | 40 | 0 | 0.8 | 40 | 0 | 100% |
| Comparative Example 3 | 100% | 0.4 | 40 | 0 | 0.4 | 40 | 0 | 0.4 | 40 | 0 | 100% |
| Comparative Example 4 | 100% | 0.4 | 20 | 0 | 0.4 | 20 | 0 | 0.4 | 20 | 0 | 100% |
| Comparative Example 5 | 100% | 0.8 | 20 | 0 | 0.8 | 20 | 0 | 0.8 | 20 | 0 | 100% |
| Comparative Example 6 | 100% | 0 | 0 | 0 | 0 | 0 | 0 | 0 | 0 | 0 | 100% |
| Comparative Example 7 | 100% | 0.8 | 0 | 0 | 0.8 | 0 | 0 | 0.8 | 0 | 0 | 100% |

Conversion rates for each reactor in Examples 1 to 3 and Comparative Examples 1 to 7 outlined in Table 1 were calculated and outlined in Table 2 below. Meanwhile, the conversion rates in each reactor were obtained by measuring the flow rate of polycarboxylic acid and alcohol put into each reactor and the flow rate of water generated in each reactor, calculating how much of the added polycarboxylic acid was reacted to generate water using the measured flow rate to calculate the conversion rates of each reactor itself, and then adding up the conversion rates up to the corresponding reactor.

TABLE 2

| | First reactor conversion rate (%) | Second reactor conversion rate (%) | Third reactor conversion rate (%) |
|---|---|---|---|
| Example 1 | 72.42 | 91.58 | 98.68 |
| Example 2 | 68.51 | 84.48 | 98.33 |
| Example 3 | 70.29 | 88.03 | 99.04 |
| Comparative Example 1 | 60.70 | 85.55 | 96.20 |
| Comparative Example 2 | 69.22 | 82.00 | 95.84 |
| Comparative Example 3 | 75.61 | 86.97 | 96.91 |
| Comparative Example 4 | 60.35 | 72.77 | 79.52 |
| Comparative Example 5 | 55.38 | 64.61 | 71.35 |
| Comparative Example 6 | 52.89 | 68.16 | 76.78 |
| Comparative Example 7 | 45.79 | 53.60 | 56.80 |

As seen in Table 2 above, when the pressure of each reactor satisfies Expressions 1 and 2, it was confirmed that a higher final conversion rate was possibly achieved. In particular, as for Comparative Examples 1 to 3 using the same amount of alcohol as Examples 1 to 3, when no pressure was applied (Comparative Example 1), or pressure was applied but maintained until the end of reaction (Comparative Examples 2 and 3), it was confirmed that a loss in the final conversion rate occurred, and as for Comparative Examples 4 to 7 using less alcohol than this, the final conversion rate failed to even reach 80% to confirm that a great deal of reaction raw materials were lost.

In addition, in Examples 2 and 3 in which pressure is controlled in the same conditions, but the amount of catalyst used is different, it was confirmed that the increase in the amount of catalyst used led to an increase in the final conversion rate, and this suggests that using an appropriate amount of catalyst in pressure control according to Expressions 1 and 2 may also lead to improvement in conversion rate.

Group 2 Confirmation of the Effect of Pressure Control in a Reaction Unit Including Four Reactors An ester-based composition was prepared in the same manner as in Group 1, except that four reactors were connected in series as a reaction unit. In each Example, the amount of catalyst put into a mixer, reactor pressure, and the amount of catalyst put into each reactor are outlined in Table 3 below, and the amount of catalyst used is described on the same basis as in Group 1 above. E values were omitted because the values remained the same at 40% in all reactors.

TABLE 3

| | Mixer | First reactor | | Second reactor | | Third reactor | | Fourth reactor | | Cat-alyst |
|---|---|---|---|---|---|---|---|---|---|---|
| | Cat-alyst | $P_1$ | Cat-alyst | $P_2$ | Cat-alyst | $P_3$ | Cat-alyst | $P_4$ | Cat-alyst | in total |
| Example 4 | 100 | 0.8 | 0 | 0.4 | 100 | 0.2 | 0 | 0 | 0 | 200 |
| Example 5 | 50 | 0.8 | 0 | 0.4 | 100 | 0.2 | 0 | 0 | 0 | 150 |

Conversion rates for each reactor in Examples 4 and 5 outlined in Table 3 above were calculated and outlined in Table 4 below. The conversion rates were calculated in the same manner as described above.

TABLE 4

| | First reactor | Second reactor | Third reactor | Fourth reactor |
|---|---|---|---|---|
| Example 4 | 66.03 | 80.23 | 90.87 | 97.26 |
| Example 5 | 71.35 | 86.97 | 90.52 | 97.97 |

As seen in Table 4, it was confirmed that even when a reaction unit having four reactors was applied, a high final conversion rate was possibly obtained as in the case of Group 1 above. When the number of reactors in the reaction unit is increased, the volume of each reactor may be made smaller, and thus the applying of the reaction unit having four reactors in this way is less costly in process design than the applying of the reaction unit having three reactors.

In addition, a rather higher initial conversion rate was achieved in Example 5 performed in the same conditions but using less catalyst, and this suggests that when the esterification reaction is performed under pressure control, a portion of the catalyst added in excess may not be involved in the initial reaction, indicating that when preparing an ester-based composition using the preparation method of the present invention, it may be advantageous to add some of the catalyst at a latter stage.

The invention claimed is:

1. A method for preparing an ester-based composition, comprising:

putting polycarboxylic acid and at least one mono-alcohol having 3 to 12 alkyl carbon atoms into a mixer to form a reaction mixture (step S1); and continuously putting the reaction mixture into a reaction unit in which a total of N reactors are connected in series to continuously produce reaction products from a first reactor to an $N^{th}$ reactor (step S2), wherein Expressions 1 and 2 below are satisfied:

$$P_{n1} \le P_{n1-1} \qquad \text{[Expression 1]}$$

$$P_1 > P_N \qquad \text{[Expression 2]}$$

$$T_m \le T_1 \le T_{n1} \qquad \text{[Expression 4]}$$

wherein in Expressions 1, 2 and 4 above, $P_N$ is a pressure of an $N^{th}$ reactor, n1 is an integer of 2 to N, N is an integer of 3 or more, $P_1$ is 0.3 barg to 1.0 barg, and $P_N$ is 0 barg to 0.5 barg $T_m$ is a temperature of the mixer, $T_N$ is a temperature of the $N^{th}$ reactor, and $T_m$ is 20 to 200° C., $T_1$ is 150 to 230° C., and $T_N$ is 180 to 250° C.

2. The method of claim 1, wherein the step S2 further satisfies Expression 3 below:

$$E_1 \le E_{n1} \qquad \text{[Expression 3]}$$

wherein in Expression 3 above, $E_N$=[{Number of moles of the mono-alcohol put into the $N^{th}$ reactor−($c$*Number of moles of the polycarboxylic acid put into the $N^{th}$ reactor)}/ ($c$*Number of moles of the polycarboxylic acid put into the first reactor)]*100% c is a number of carboxylic acid groups contained in one molecule of the polycarboxylic acid.

3. The method of claim 1, further comprising at least one step selected from the group consisting of:

adding a catalyst to the reaction mixture between the step S1 and the step S2;

adding the catalyst to the polycarboxylic acid and the mono-alcohol before the step S1; and adding the catalyst to the first reactor of the step S2.

4. The method of claim 3, further comprising adding the catalyst to at least one reactor selected from among the second to $N^{th}$ reactors of the step S2.

5. The method of claim 3, wherein a catalyst is tetraalkyl titanate.

6. The method of claim 2, wherein $E_1$ is 0 to 100%, and $E_N$ is 0 to 200%.

7. The method of claim 1, wherein N is an integer of 3 to 5.

8. The method of claim 1, further comprising:

continuously moving the reaction products into a separation unit to remove unreacted alcohol (step S3); and

putting the unreacted alcohol removed from the separation unit back into at least one reactor selected from among the reactors of the reaction unit (step S4).

9. The method of claim 8, further comprising putting at least one mono-alcohol having 3 to 12 alkyl carbon atoms into the reaction products from which the unreacted alcohol is removed to perform a trans-esterification reaction (step S5), wherein the alcohol input in the step S5 is different from the alcohol input in the step S1.

10. The method of claim 1, wherein the polycarboxylic acid is at least one selected from the group consisting of a dicarboxylic acid, a tricarboxylic acid, and a tetracarboxylic acid.

11. The method of claim 10, wherein:

the dicarboxylic acid is at least one selected from the group consisting of a linear dicarboxylic acid having 2 to 10 carbon atoms, a terephthalic acid, a phthalic anhydride, an isophthalic acid, a cyclohexane dicarboxylic acid and an anhydride thereof;

the tricarboxylic acid is at least one selected from the group consisting of a citric acid, a trimellitic acid, a cyclohexane tricarboxylic acid and an anhydride thereof; and the tetracarboxylic acid is at least one selected from the group consisting of a benzenetetracarboxylic acid, a furantetracarboxylic acid, a cyclohexane tetracarboxylic acid, a tetrahydrofuran tetracarboxylic acid aid an anhydride thereof, and a derivative thereof.

* * * * *